US008210181B2

(12) United States Patent
Gunaratnam et al.

(10) Patent No.: US 8,210,181 B2
(45) Date of Patent: *Jul. 3, 2012

(54) MASK AND HEADGEAR CONNECTOR

(75) Inventors: Michael Kassipillai Gunaratnam, Marsfield (AU); Philip Rodney Kwok, Chatswood (AU)

(73) Assignee: ResMed Limited, Bella Vista (AU)

( * ) Notice: Subject to any disclaimer, the term of this patent is extended or adjusted under 35 U.S.C. 154(b) by 162 days.

This patent is subject to a terminal disclaimer.

(21) Appl. No.: 12/537,663

(22) Filed: Aug. 7, 2009

(65) Prior Publication Data

US 2009/0293869 A1 Dec. 3, 2009

Related U.S. Application Data

(63) Continuation of application No. 10/090,173, filed on Mar. 6, 2002, now Pat. No. 7,600,513, which is a continuation of application No. 09/504,220, filed on Feb. 15, 2000, now Pat. No. 6,374,826, which is a continuation-in-part of application No. 29/115,618, filed on Dec. 16, 1999, now Pat. No. Des. 443,355.

(30) Foreign Application Priority Data

Jun. 18, 1999 (AU) .................................. 1916/99
Jun. 18, 1999 (AU) .................................. PQ1040

(51) Int. Cl.
*A62B 18/08* (2006.01)
*A62B 18/02* (2006.01)
*A62B 18/00* (2006.01)
*A62B 9/04* (2006.01)

(52) U.S. Cl. ......... 128/207.11; 128/206.27; 128/206.21; 128/205.25; 128/202.27; 128/200.24

(58) Field of Classification Search .................. 128/857, 128/863, 200.24, 201.22, 201.23, 201.24, 128/201.25, 201.26, 202.11, 203.29, 204.11, 128/204.29, 205.25, 206.12, 206.13, 206.16, 128/206.18, 206.21, 206.27, 206.28, 207.11, 128/207.13; 24/614–616, 30.55, 30.51, 336, 24/572.1, 573.1, 581.1, 578.1; 36/50.1, 50.5
See application file for complete search history.

(56) References Cited

U.S. PATENT DOCUMENTS

| 2,097,676 A | 11/1937 | Shindel et al. |
| 2,292,568 A | 8/1942 | Kanter et al. |
| 2,823,671 A | 2/1958 | Garelick |
| 2,928,387 A | 3/1960 | Layne |

(Continued)

FOREIGN PATENT DOCUMENTS

AU  A-59430/94  10/1995

(Continued)

OTHER PUBLICATIONS

European Search Report filed in EP 05026584.2 (Jan. 27, 2006).

(Continued)

*Primary Examiner* — Annette Dixon
(74) *Attorney, Agent, or Firm* — Nixon & Vanderhye P.C.

(57) ABSTRACT

A connector arrangement joining a respiratory mask and headgear is adapted for single-handed disengagement by the patient. A first, rigid connector part is formed into the rigid mask frame, with a mating second connector attached to a strap of the headgear. The connectors are held away from the patient's face by the connection to the mask frame.

22 Claims, 8 Drawing Sheets

U.S. PATENT DOCUMENTS

| | | | |
|---|---|---|---|
| 4,414,973 A * | 11/1983 | Matheson et al. | 128/206.15 |
| 4,437,462 A | 3/1984 | Piljay et al. | |
| 4,802,262 A | 2/1989 | Kasai | |
| 4,848,334 A * | 7/1989 | Bellm | 128/207.11 |
| 4,928,364 A | 5/1990 | Ikeda | |
| D310,431 S * | 9/1990 | Bellm | D24/110.4 |
| 5,033,171 A * | 7/1991 | Kasai | 24/614 |
| 5,069,205 A | 12/1991 | Urso | |
| 5,205,832 A | 4/1993 | Tuman | |
| 5,243,971 A | 9/1993 | Sullivan et al. | |
| 5,245,993 A | 9/1993 | McGrady et al. | |
| 5,263,234 A | 11/1993 | Fudaki | |
| 5,291,880 A | 3/1994 | Almovist et al. | |
| 5,396,881 A | 3/1995 | Klein | |
| 5,555,569 A | 9/1996 | Lane | |
| 5,657,493 A * | 8/1997 | Ferrero et al. | 2/428 |
| 5,662,101 A | 9/1997 | Ogden et al. | |
| 5,746,201 A * | 5/1998 | Kidd | 128/206.24 |
| 5,884,624 A | 3/1999 | Barnett et al. | |
| 5,918,598 A | 7/1999 | Belfer et al. | |
| 5,921,239 A | 7/1999 | McCall et al. | |
| 5,924,420 A * | 7/1999 | Reischel et al. | 128/206.21 |
| 5,996,192 A | 12/1999 | Haines et al. | |
| 6,192,886 B1 | 2/2001 | Rudolph | |
| 6,199,219 B1 | 3/2001 | Silken et al. | |
| D443,355 S | 6/2001 | Gunaratnam et al. | |
| 6,374,826 B1 | 4/2002 | Gunaratnam et al. | |
| 6,412,488 B1 * | 7/2002 | Barnett et al. | 128/207.13 |
| 2003/0106557 A1 | 6/2003 | Viljanen et al. | |
| 2003/0178026 A1 | 9/2003 | Byram | |
| 2004/0025883 A1 | 2/2004 | Eaton et al. | |
| 2004/0045551 A1 | 3/2004 | Eaton et al. | |
| 2004/0112384 A1 | 6/2004 | Lithgow et al. | |
| 2005/0011521 A1 | 1/2005 | Sprinkle et al. | |
| 2005/0022820 A1 | 2/2005 | Kwok et al. | |
| 2005/0076912 A1 | 4/2005 | Eifler et al. | |
| 2005/0126573 A1 | 6/2005 | Jaffre et al. | |
| 2005/0172969 A1 | 8/2005 | Ging et al. | |
| 2006/0076019 A1 | 4/2006 | Ho | |
| 2006/0096598 A1 | 5/2006 | Ho et al. | |
| 2006/0162729 A1 | 7/2006 | Ging et al. | |
| 2006/0196509 A1 | 9/2006 | Drew et al. | |

FOREIGN PATENT DOCUMENTS

| | | |
|---|---|---|
| EP | 0958841 A2 | 11/1999 |
| FR | 2727836 | 6/1996 |
| GB | 684788 | 12/1952 |
| GB | 704167 | 2/1954 |
| GB | 2293410 | 3/1996 |
| WO | WO 87/01950 | 4/1987 |
| WO | WO 97/20597 | 6/1997 |
| WO | WO 98/48878 | 11/1998 |

OTHER PUBLICATIONS

Extended European Search Report Mailed Jan. 24, 2011 in European Appln. No. 10185014.7.

* cited by examiner

MASK AND HEADGEAR CONNECTOR

CROSS-REFERENCES TO RELATED APPLICATIONS

This application is a continuation of U.S. application Ser. No. 10/090,173, filed Mar. 6, 2002, now U.S. Pat. No. 7,600,513, which is a continuation of U.S. application Ser. No. 09/504,220, filed Feb. 15, 2000, now U.S. Pat. No. 6,374,826, which is a Continuation-In-Part of U.S. Design application No. 29/115,618, filed Dec. 16, 1999, now Design Pat. No. 443,355, the specifications and drawings of which are incorporated herein by reference.

FIELD OF THE INVENTION

The invention relates to a connector for use with a mask and headgear suitable for the delivery of breathable gases to a patient for the treatment of sleep disordered breathing (SDB).

BACKGROUND OF THE INVENTION

Respiratory masks used in the treatment of SDB may comprise either a nasal mask, designed to fit over a patient's nose, or a full face mask designed to fit over the nose and mouth of the patient. Air or other breathable gas is supplied by a blower and passed along a flexible conduit to the mask.

The mask generally comprises a relatively rigid shell, termed a frame, which defines a rearwardly opening cavity covering the patient's nose and/or mouth and a soft portion, termed a cushion, which spaces the frame away from the face for comfortable contact.

The masks are typically held in place using headgear, the mask and headgear being joined using some form of connector.

One known example is the Mirage® Mask (ResMed Limited), shown in FIG. 1. In this case, the headgear 100 is constructed from fabric and includes a rear portion, which engages the region near the occiput of the patient, and four straps 110 which are secured to a forehead support 120 (2 straps) and nasal mask frame 130 (2 straps). The straps include hook and loop material, such as Velcro™ on one side. The mask frame and forehead supports include loops 140 through which a strap can pass. In order to secure the mask in place on a patient's head, the four straps are passed through the four corresponding loops and held in place at an appropriate length by the hook and loop material. The patient can adjust the length of the material in order to secure a good fit of the mask. In some cases, it can require considerable adjustment to find the optimal length of straps which is required. A difficulty with this connector is that if the patient removes the mask by loosening the straps, they will lose what may have been a good fit of the mask the next time it is being used. In this case they will need to repeat the adjustment step.

Another known manner of connecting the mask and headgear is shown in FIGS. 2a, 2b and 2c. In this headgear, a short strap length 200 is secured to one side of the mask, with a two-part, press-release connector 210, 220 attaching this to the strap 250 of the headgear. One disadvantage of the approach of using this arrangement is that the connector may be difficult to release because the connector is free to move relative to the mask frame. A further disadvantage of this arrangement is that the connector may be in contact with the patient's face which may lead to discomfort in use, particularly if they sleep on their side.

More detailed views of this prior art connector are shown in FIGS. 2b and 2c. Each part of the connector includes a bar 230, 240 behind which a respective one of the straps 200, 250 may be passed. The male portion 220 of the connector includes a resilient cantilever 260 which is captured behind a bar 270 on the female portion 210. The cantilever is depressed to engage and disengage the connector. A further disadvantage of this particular connector, best seen in FIG. 2b, is that it may be awkward to disengage the connector because of the close positioning of the bar 270 to the cantilever 260.

Another known mask and headgear connector is shown in FIG. 3a to FIG. 3d. This comprises a flexible part 310 positioned on the outer surface of a flexible mask frame 300 and a rigid part 320 formed generally as a D-ring with a loop to which the headgear strap is attached. The flexible part consists of a base 330 supporting an upper portion 340 (best illustrated in FIG. 3a) which overhangs the base portion 330 and has a narrow central region 350. In order to engage and disengage the connector, the flexible part 310 must be deformed whilst the D-ring of the rigid part is pushed over the upper portion 340 to engage below the overhanging ledge. This arrangement is awkward to engage and disengage and typically requires two hands.

Another known mask and headgear connector consists of hooks on the end of the headgear straps and corresponding holes in the mask frame. To engage the mask and headgear connector, the hook is passed through one of the corresponding holes on the headgear. This arrangement is also awkward to engage and disengage and typically requires two hands. Also, it is possible for the hooks to disengage during sleep as there is no locking means for the connection.

There is a need for a connector arrangement which is simple and quick to operate.

SUMMARY OF THE INVENTION

The invention provides, in one form, a respiratory mask and headgear combination comprising a respiratory mask having a rigid mask frame, adjustable headgear for securing said mask on a patient, said headgear including at least one attachment strap, said mask frame having rigidly secured thereto a rigid first connector, further comprising a second connector adapted for releasable mating with said first connector, said second connector having means for connection of said attachment strap of the headgear.

The invention further provides a respiratory mask and headgear combination adopted for single-handed disengagement, comprising a rigid mask frame, adjustable headgear for securing said mask on a patient, said headgear including at least one attachment strap, said mask frame having rigidly secured thereto a rigid first connector, further comprising a second connector connected to said strap of said headgear, said second connector being adapted for releasable mating with the first connector and having first and second gripping surfaces positioned for gripping of said second connector between a thumb and finger of a patient's hand and release means positioned for operation by another finger of the patient's hand.

BRIEF DESCRIPTION OF THE DRAWINGS

Further embodiments of the invention will now be described with reference to the accompanying drawings, in which:

FIG. 2b shows further detail of the prior art mask and headgear connector shown in FIG. 2a.

FIG. 6b shows a side view of FIG. 6a.

FIG. 6c shows a sectional view along A-A of FIG. 6a.

FIG. 6d shows a perspective view of FIG. 6a.

DETAILED DESCRIPTION OF THE INVENTION

Figure 1:
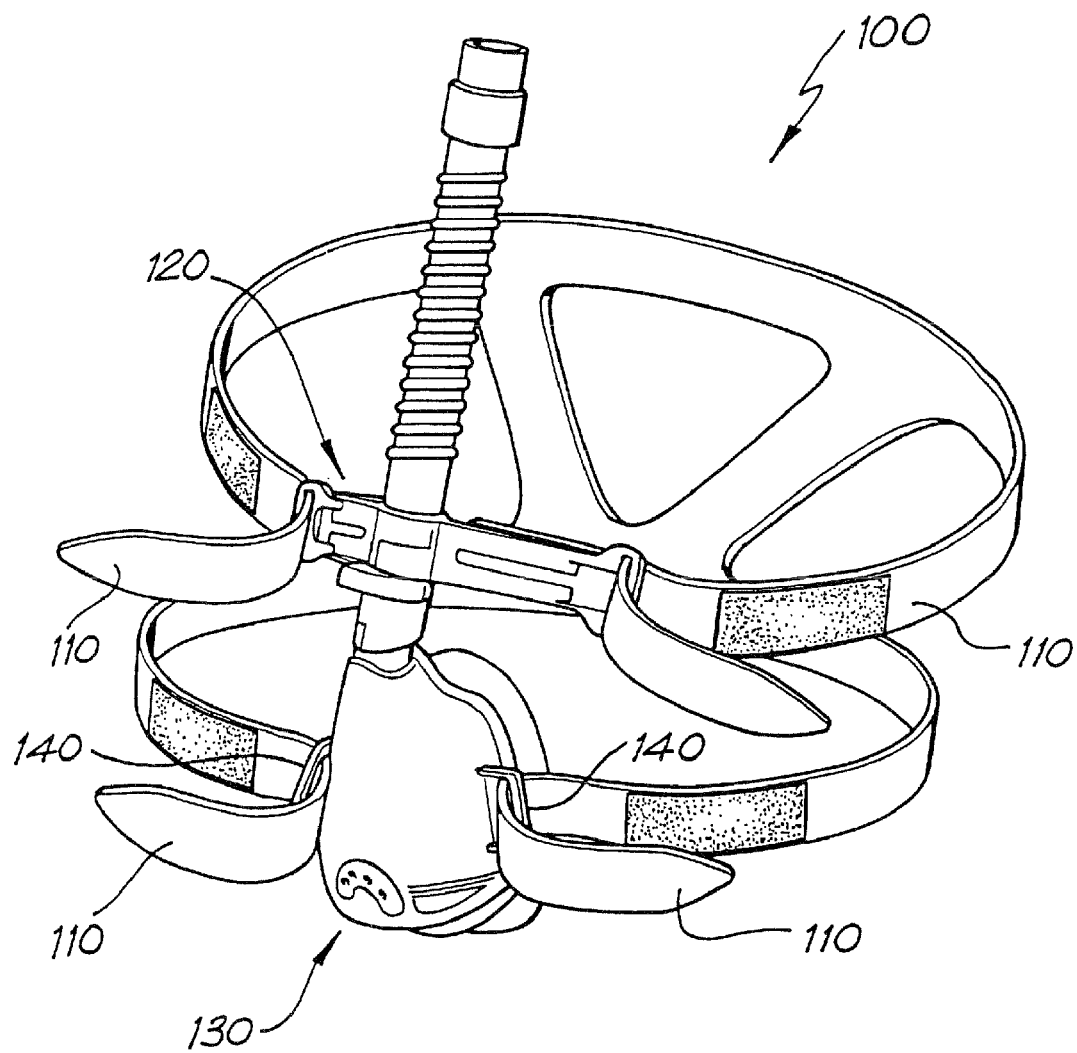
FIG. 1 shows the prior art Mirage® mask and headgear assembly.
Figure 2A:
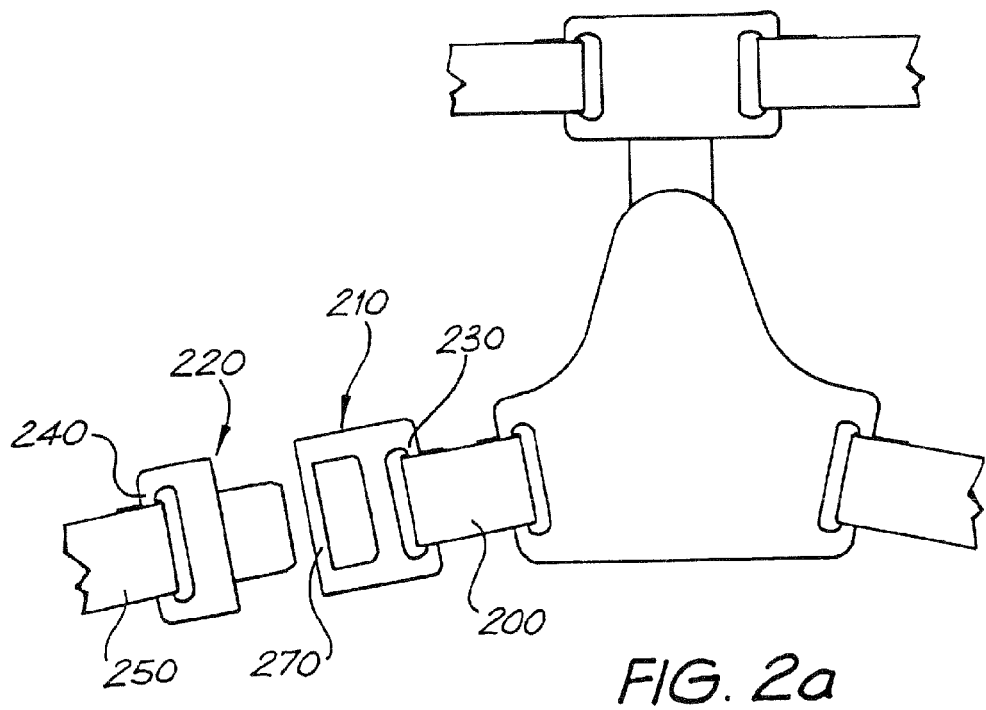
FIG. 2a shows a front view of a prior art mask and headgear assembly.
Figure 2B:
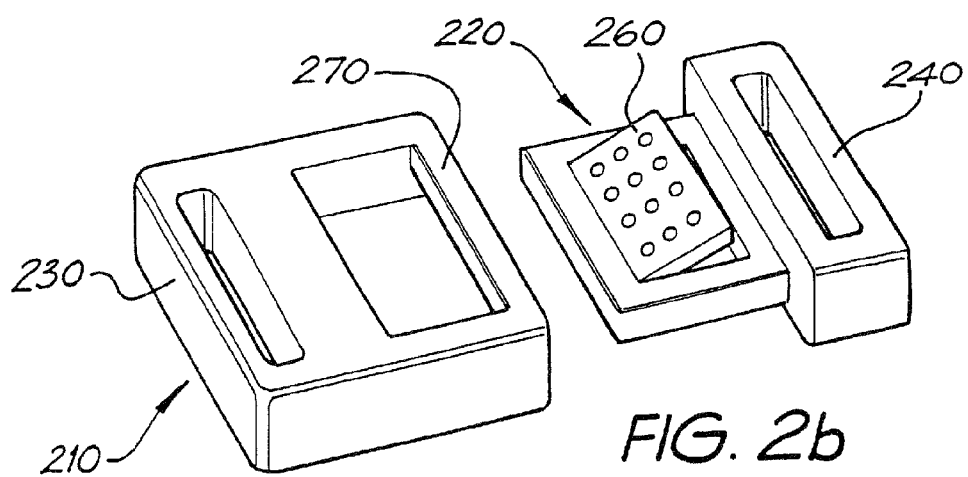
Figure 2C:
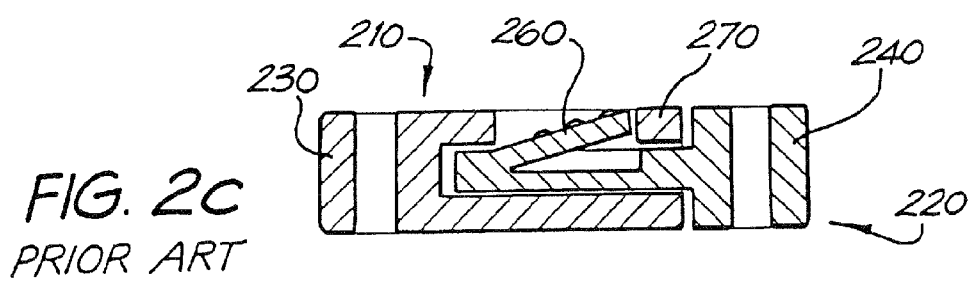
FIG. 2c shows a cross-sectional view of the prior art mask and headgear connector shown in FIG. 2b.
Figure 3A:
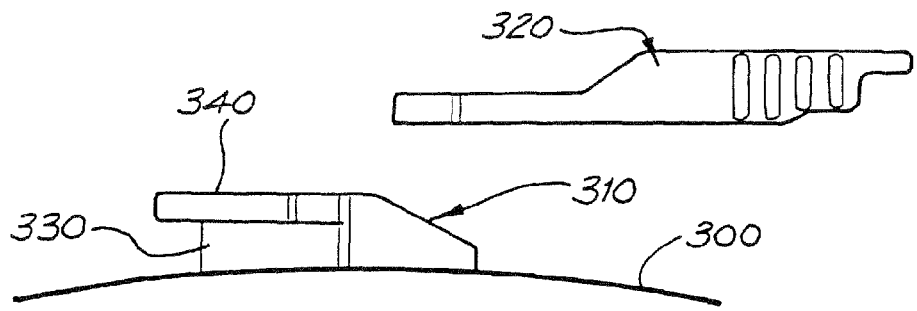
FIG. 3a shows a side view of another prior art mask and headgear connector where the two parts are not engaged.
Figure 3B:
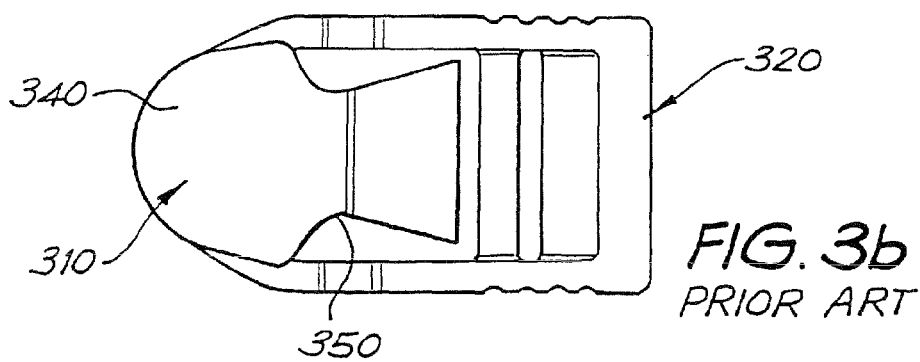
FIG. 3b shows a top view of the prior art connector shown in FIG. 3a, where the two parts are engaged.
Figure 3C:
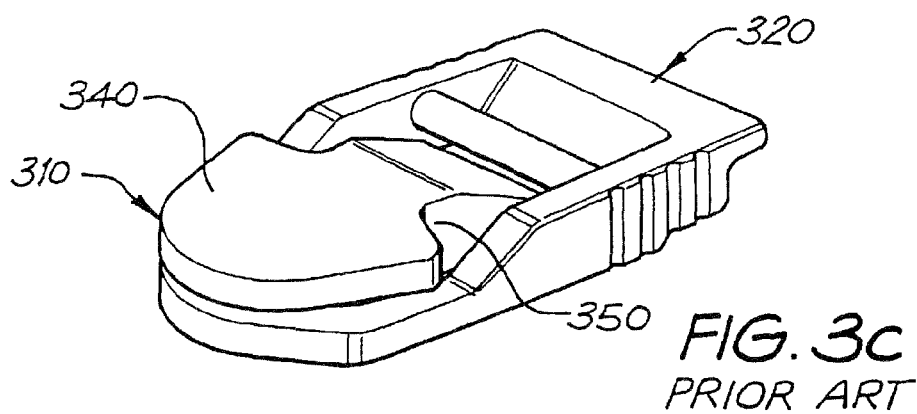
FIG. 3c shows a perspective view of the prior art connector shown in FIG. 3a, where the two parts are engaged.
Figure 3D:
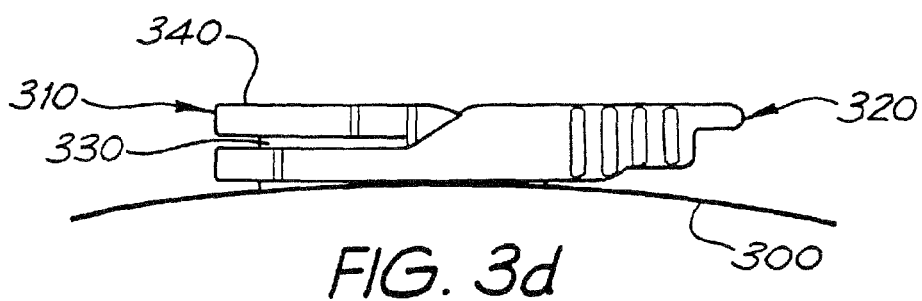
FIG. 3d shows a side view of the prior art connector shown in FIG. 3a, where the two parts are engaged.
Figure 4:
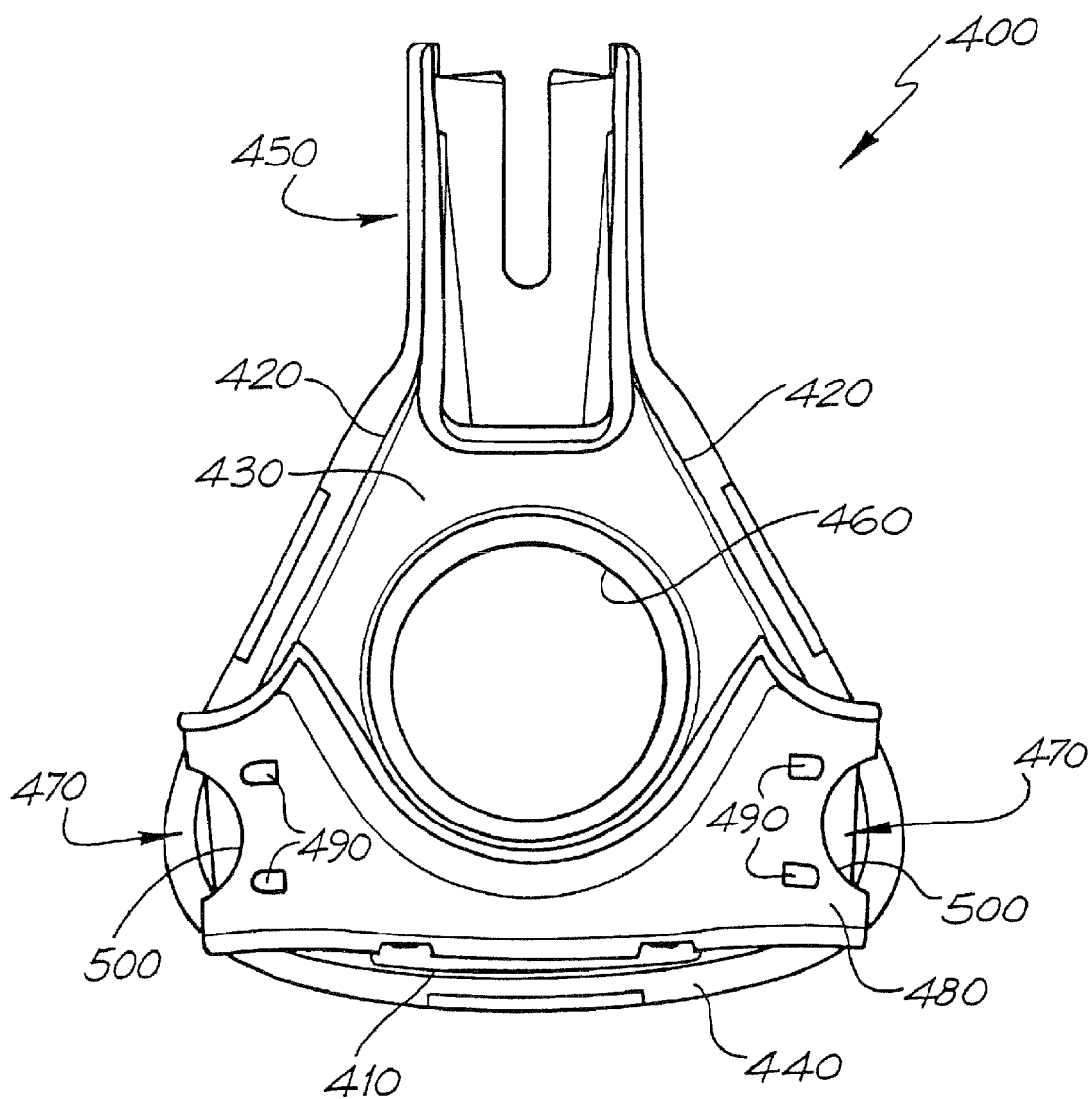
FIG. 4 shows a front view of a mask frame incorporating a female portion of the connector according to one embodiment of the invention.
Figure 5:
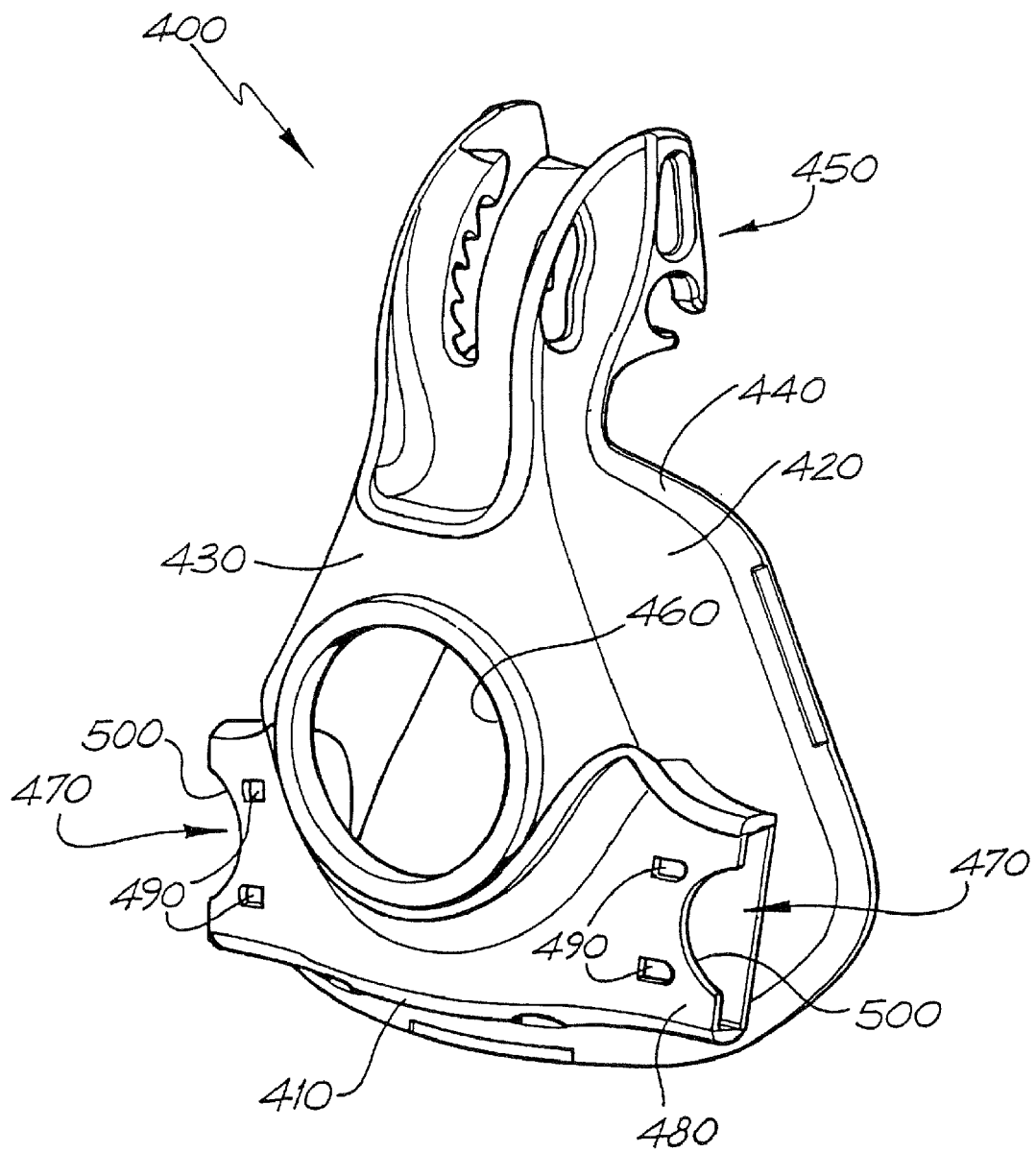
FIG. 5 shows a perspective view of the mask frame of FIG. 4.
Figure 6A:
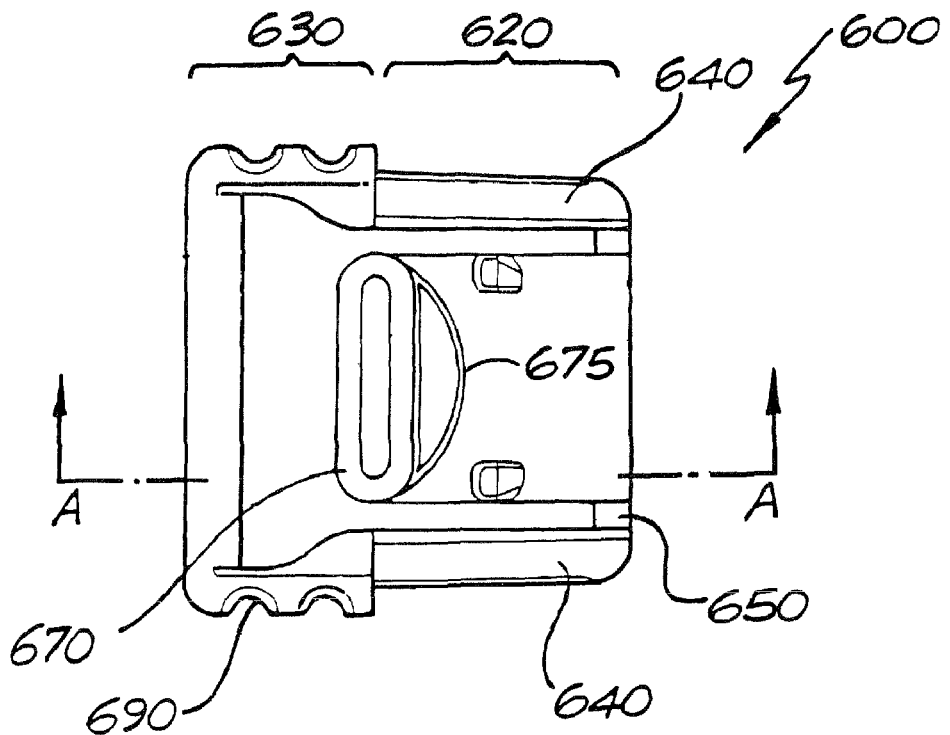
FIG. 6a shows a front view of a male portion of the connector adapted for use with the mask frame of FIGS. 4 and 5.
Figure 6B:
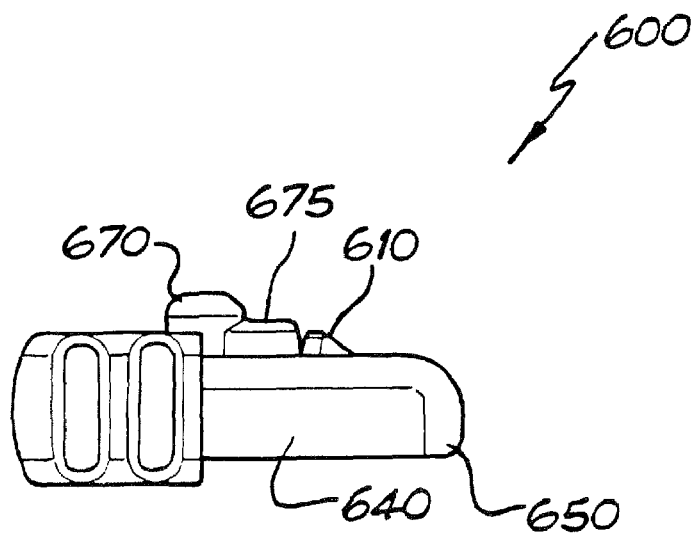
Figure 6C:
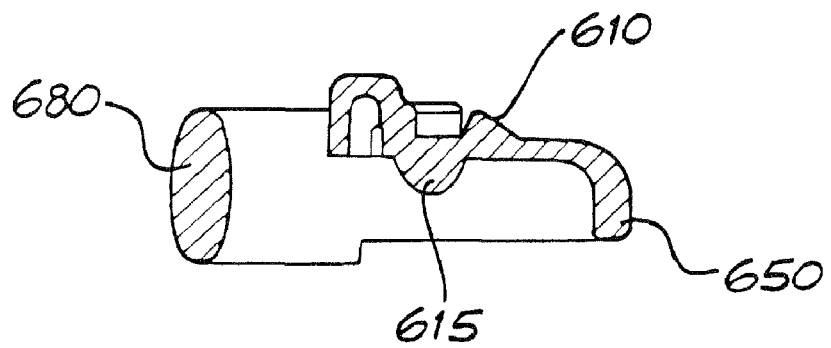
Figure 6D:
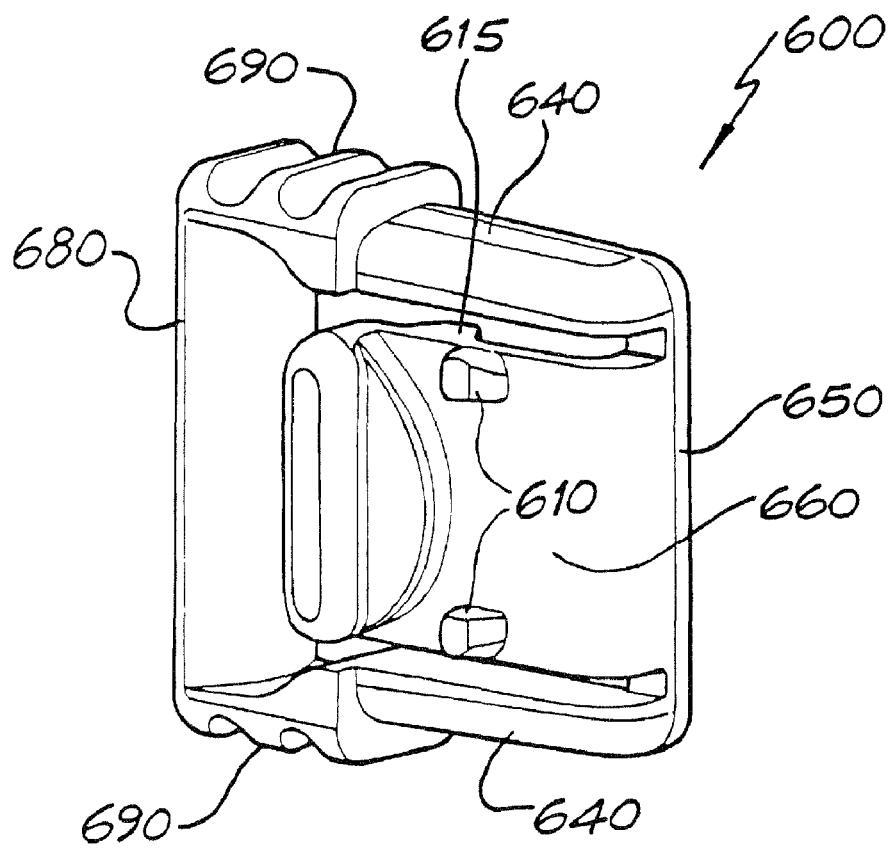

FIGS. 4 and 5 illustrate a mask frame 400 for a nasal mask, formed as a moulded shell of polycarbonate or similar rigid material, which acts as a body onto which the other components of the mask are attached.

The frame 400 is generally triangular in front view, having a base 410, a pair of inclined side walls 420 extending towards an apex and a front wall 430. The frame defines a mask cavity covering the patient's nose, and is open at its rear. A rim 440 at the rear edge of the base 410 and side walls 420 approximates the contours of the patient's face and is adapted for attachment of a soft mask cushion (not shown) to space the frame away from the patient's face for sealing and comfort. The apex of the frame has an extension 450 for attachment of a forehead support (not shown).

In the illustrated mask frame, a gas inlet aperture 460 is formed in the front wall 430, for connection of a gas supply conduit or similar, which may include an elbow connector (not shown) pivotably connected to the frame. In other forms of mask, the gas inlet aperture may be formed at the apex of the frame.

Integrally moulded into the lower corner regions of the rigid mask frame are a pair of female connector parts 470, for receiving the leading portions of the male connector parts 600, 700 illustrated in FIGS. 6a to 6d, or FIGS. 7a and 7b. These female connector parts open generally to the side of the mask, but are angled slightly downwards and rearwards (relative to the orientation of the mask frame) so that they hold the male connectors approximately parallel to that part of the patient's cheek region which the connectors overlie. The connectors are held clear of the patient's face by the rigid mask frame 400.

The female connectors 470 each define a recess which opens towards a side of the mask and which approximates a rounded-cornered rectangular in end view, adapted to provide a close fit with the corresponding male connectors 600,700 when engaged. These end shapes are preferably slightly asymmetric (keyed) so as to prevent upside-down insertion of the male connector.

A front wall 480 of the female connector has a pair of sockets 490 at least on its inner surface, for receiving respective lugs 610 of the male connector 600. The end of the front wall may also have a curved cut-out portion 500, as will be described below.

A corresponding male connector part 600 is illustrated in FIGS. 6a to 6d.

The male connector has a leading portion 620 which is received in the recess of the female connector 470, and a trailing portion 630 which remains outside the recess. The leading portion includes upper and lower side beams 640 connected by a cross-piece 650 at their leading ends, and a resiliently biased cantilever member 660 depending from the cross-piece 650 and extending back towards the trailing portion. The cantilever has on its front surface the lugs 610, and a ridge 670 at its trailing edge. The cantilever has on its back surface an arcuate projection 615 at a position between the lugs 610 and the ridge 670.

The locating lugs 610 have a rounded wedge profile so as to allow reduce wear and provide smooth engagement. The wedge profile does allow insertion of the male connector 600 into the female connector 470 on the mask without depression of the cantilever, although in preferred operation the patient will depress the cantilever by pushing on ridge 670 for both engagement and disengagement. Once the male connector has been inserted sufficiently to snap the locating lugs 610 into engagement with corresponding sockets 490 of the female connector, disengagement can occur only by depression of the cantilever.

The trailing portion 630 of the male connector has a cross-bar 680 forming a loop through which the headgear strap can be passed and adjusted for proper fit. Upper and lower sides 690 of the trailing portion have grooves or other formations to make it more easily gripped by the patient's fingers, while the distance between the leading side of the cross-bar 680 and the trailing edge and ridge 670 of the cantilever is preferably at least 5 mm to allow easy connection of the strap and provide sufficient space for a finger to push on the cantilever ridge, even when the strap is attached. The arcuate cut-out 500 in the female connector front wall is configured to contact an arcuate ridge 675 of the male connector 660 in the connected state and allows clearance for an end of the finger to overhang the ridge 670 when the ridge is being contacted by the pad of the finger.

Figure 7A:
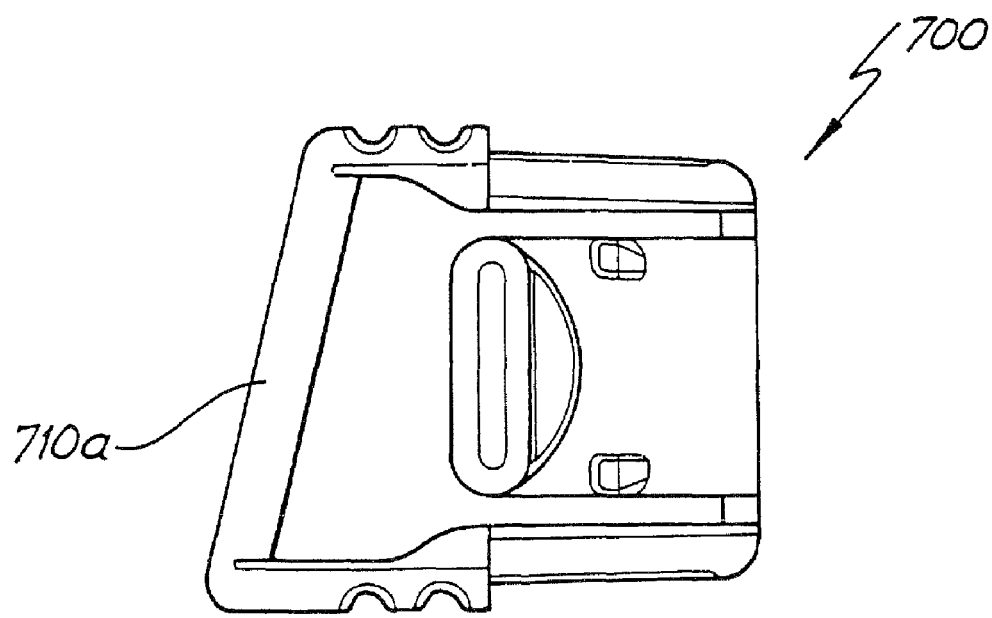
FIGS. 7a and 7b show an embodiment of the invention where the cross-bar on the male portions of the connectors have different angles.
Figure 7B:
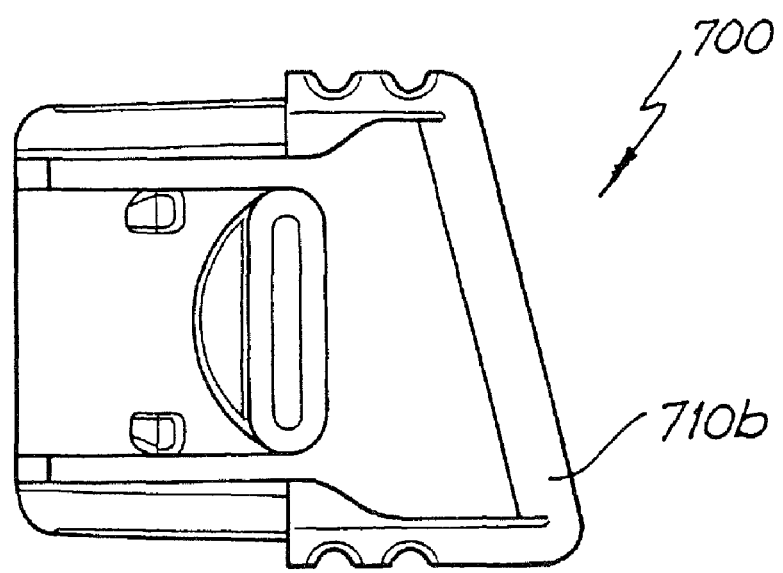

FIGS. 7a and 7b illustrate a male connector 700 which is a variation on that of FIGS. 6a to 6d, in that the cross bars 710a, 710b for attachment of the headgear strap are set at an angle.

The shape, dimensions and position of the connectors may be optimised for most convenient use. For example, the male connector may be approximately 20 mm wide, 25 mm long and 10 mm thick. The cantilever 660 is approximately 15 mm long. The locating lugs 610 are approximately 3 mm long, 2 mm wide and 1 mm high, and the ridge is approximately 14 mm wide and has a length of approximately 5 mm.

The female connectors 470 are oriented on the mask frame so that in use the straps of the headgear are aligned to be approximately parallel with the sides of the face with which they make contact. When viewed from the front of the mask (the view in FIG. 4), the tops of the left and right hand side male connector's cross-bars 680 are further apart than the bottoms of the cross-bars. When viewed from the top the mask, the connectors are aligned to be positioned on an arc of an ellipse. An advantage from this arrangement is that when straps are connected and tensioned, the line of force will be more evenly transferred from the mask to the frame.

Both portions of the connector are preferably constructed from polycarbonate, such as Makrolon 2458 polycarbonate from Bayer, or similar rigid plastics material. The female portions of the connectors are clear and desirably are integrally moulded with the mask frame which is formed of the same polycarbonate material, thus ensuring a permanent, rigid attachment of the female connector to the mask frame and minimising the number of separate parts. The male portions may be frosted or textured. An advantage from using a frosted or slightly textured surface is that the male portion may be easier to distinguish from the female portion by touch. This is an advantage in the dark, the typical time when the mask is being used by a patient.

The configuration thus allows single-hand operation of the connector using, for example, thumb and index finger to grip the grooved sides 690 of the male connector and the middle finger to depress the cantilever. The connectors may be located on both the left and right hand side of the mask. In this way persons may use which ever side is most convenient to them. Alternatively the frame may be formed with only one connector, to reduce manufacturing costs.

In one unillustrated embodiment, the press release mechanism may be adapted to be operated by pressing the top and/or bottom sides of the male connector.

By rigidly forming one part of the connector onto the mask frame, the patient does not need to use both hands to disconnect the mask for removal. Thus, the arrangement facilitates quick and easy disconnection even though the connector will be out of patient's line of vision and the patient may be less than fully awake or in an anxious state.

A further advantage of using female portions 470 integrated with the mask frame is that they result in a reduced dead volume of the mask frame.

While particular embodiments of this invention have been described, it will be evident to those skilled in the art that the present invention may be embodied in other specific forms without departing from the essential characteristics thereof. The present embodiments and examples are therefore to be considered in all respects as illustrative and not restrictive, the scope of the invention being indicated by the appended claims rather than the foregoing description, and all changes which come within the meaning and range of equivalency of the claims are therefore intended to be embraced therein.

The invention claimed is:

1. A respiratory mask and headgear combination comprising:
   a respiratory mask having a rigid mask frame having a front wall and defining a cavity configured to cover at least a nose of a patient, the front wall having an inlet aperture,
   adjustable headgear for securing said mask on the patient, said headgear including at least one attachment strap, said mask frame having rigidly secured thereto a rigid first connector portion, and
   a second connector portion adapted for releasable mating with said first connector portion, wherein
   said first and second connector portions form a press-release connection between said mask frame and said strap;
   said first connector portion is a female connector formed in one piece with said mask frame on the front wall of the cavity adjacent the inlet aperture; and
   said second connector portion is a corresponding male connector.

2. A respiratory mask and headgear combination according to claim 1, wherein the male connector portion includes a resiliently biased cantilever member depending from a leading end portion of said male connector portion.

3. A respiratory mask and headgear combination according to claim 2, wherein said cantilever member has a leading end, a trailing end, a locking portion, located intermediate said leading end and trailing end, structured to engage with said first connector portion, and release portion located adjacent said trailing end.

4. A respiratory mask and headgear combination according to claim 3, wherein said release portion comprises a raised portion adjacent a trailing end of said cantilever member.

5. A respiratory mask and headgear combination according to claim 4, wherein a space is provided immediately behind said trailing end of the cantilever member.

6. A respiratory mask and headgear combination according to claim 3, wherein said locking portion comprises at least one lug on a forward surface of said cantilever member, said lug engaging a corresponding socket of said first connector portion.

7. A respiratory mask and headgear combination according to claim 1, wherein said first and second connector portions are structured to be spaced forwardly of the patient's face by the front wall of said rigid mask frame.

8. A respiratory mask for use with a headgear having male connector portions thereon, each of the male connector portions including at least one resiliently biased locking element, the respiratory mask comprising:
   a mask frame, wherein the mask frame includes a front wall portion defining a forward end of the mask frame, the front wall portion having a circular gas inlet aperture configured to connect to a gas delivery conduit; and
   a pair of female connector portions formed in one piece with the mask frame and being configured to receive the male connector portions therein.

9. A respiratory mask according to claim 8, wherein the mask frame including a pair of inclined side wall portions and a base portion, each of the side wall portions and the base portion having a portion thereof connected to the front wall portion.

10. A respiratory mask according to claim 9, wherein the mask frame includes a rim at rear edges of the inclined side wall portions and the base portion, the rim defining a rearward end of the mask frame and being configured to allow a cushion to be attached thereto.

11. A respiratory mask according to claim 9, wherein each of the female connector portions includes a generally oblong slot, each generally oblong slot being formed by a first wall structure that is disposed between respective side wall portions and the base portion, a pair of parallel spaced opposing wall structures extending generally perpendicularly from the first wall structure and a second wall structure extending between and connected to the pair of spaced opposing wall structures, the second wall structure being spaced from and generally parallel to the first wall structure, each of the first and second wall structures and the pair of spaced opposing wall structures having an inward end portion and an outward end portion defining a direction that extends generally radially outwardly relative to the circular gas inlet aperture, the outward end portions defining the generally oblong slot therebetween.

12. A respiratory mask according to claim 11, wherein the second wall structure includes at least one recess extending therethrough configured to cooperate and receive the at least one resiliently biased locking element of the respective male connector portions, the at least one recess being formed adjacent each generally oblong slot.

13. A respiratory mask and headgear combination, comprising:
   a respiratory mask having a rigid mask frame having a front wall and defining a cavity configured to cover at least a nose of a patient, the front wall having an inlet aperture, adjustable headgear for securing said mask on a patient, said headgear including at least one attachment strap, whereby said mask has a female connector portion, made of a rigid material and permanently attached to the mask frame, and a male connector portion adapted for releasable mating with said female connector portion, said male connector portion having a cross bar forming a loop through which the attachment strap can be passed and adjusted for proper fit, wherein said male connector portion is at least partially insertable into the female connector portion to form a snap-fit locked connection between the female and male connector portions, and wherein the male connector portion includes a press-release mechanism having at least one depressible portion to allow single-handed disengagement by the patient in use, wherein said female and male connector portions are adjacent the inlet aperture in the front wall.

14. A respiratory mask and headgear combination according to claim 13, wherein said press-release mechanism comprises a resiliently biased cantilever member having means for releasable locking engagement between the male and female connector portions.

15. A respiratory mask and headgear combination according to claim 14, wherein said cantilever member has a leading end, a trailing end, locking means located intermediate said leading end and trailing end portion, and release means located adjacent said trailing end.

16. A respiratory mask and headgear combination according to claim 15, wherein said release means comprises a raised portion adjacent a trailing end of said cantilever member.

17. A respiratory mask and headgear combination according to claim 16, wherein a space is provided immediately behind said trailing end of the cantilever member.

18. A respiratory mask and headgear combination according to claim 15, wherein said locking means comprises at least one lug on a forward surface of said cantilever member, said lug engaging a corresponding socket.

19. A respiratory mask and headgear combination according to claim 13, wherein said press-release mechanism includes a pair of lugs mounted on a flexible cantilever member and a pair of sockets structured to selectively release the respective lugs.

20. A respiratory mask and headgear combination according to claim 13, wherein each said female connector portion is configured and positioned to open generally to the lateral side of the mask.

21. A respiratory mask and headgear combination according to claim 13, wherein said female connector portion is rigidly secured to said mask frame.

22. A respiratory mask and headgear combination according to claim 13, in which the attachment strap may be detached from the frame via the male connector portion without detaching the strap from the male connector portion.

* * * * *